United States Patent [19]
Berger et al.

[11] Patent Number: 5,674,222
[45] Date of Patent: Oct. 7, 1997

[54] FORKED PLATE

[75] Inventors: Roger Berger, Buren; Peter E. Ochsner, Frenkendorf, both of Switzerland; Thomas Welte, Weil, Germany

[73] Assignee: Synthes (U.S.A.), Paoli, Pa.

[21] Appl. No.: 495,607

[22] PCT Filed: Jun. 1, 1994

[86] PCT No.: PCT/CH94/00102
§ 371 Date: Nov. 6, 1995
§ 102(e) Date: Nov. 6, 1995

[87] PCT Pub. No.: WO95/32674
PCT Pub. Date: Dec. 7, 1995

[51] Int. Cl.⁶ .................................................. A61B 17/76
[52] U.S. Cl. ........................................... 606/69; 606/65
[58] Field of Search .......................... 606/60, 61, 69, 606/70, 71, 72, 73, 74, 65, 67, 75

[56] References Cited

U.S. PATENT DOCUMENTS 3,256,877 6/1966 Haboush ........................... 606/67
4,838,252 6/1989 Klaue ............................... 606/69
4,905,680 3/1990 Tunc ................................ 606/69

FOREIGN PATENT DOCUMENTS

| 0009327 | 4/1980 | European Pat. Off. |
| 1487486 | 5/1967 | France. |
| 2606268 | 5/1988 | France. |
| 18 13 807 | 6/1969 | Germany. |
| 26 02 900 | 7/1977 | Germany. |

*Primary Examiner*—Michael Buiz
*Assistant Examiner*—David O. Reip
*Attorney, Agent, or Firm*—Fish & Richardson P.C.

[57] ABSTRACT

A bone plate is disclosed having a longitudinal shaft section with boreholes to admit attachment screws. Two forklike prongs are attached to the shaft section. The prongs are bent relative to the longitudinal axis of the shaft section at an angle from 60 degrees to 150 degrees. The prongs can be lengthened individually so that the bone plate can be adjusted to different applications, even interoperatively, and without great expense.

28 Claims, 4 Drawing Sheets

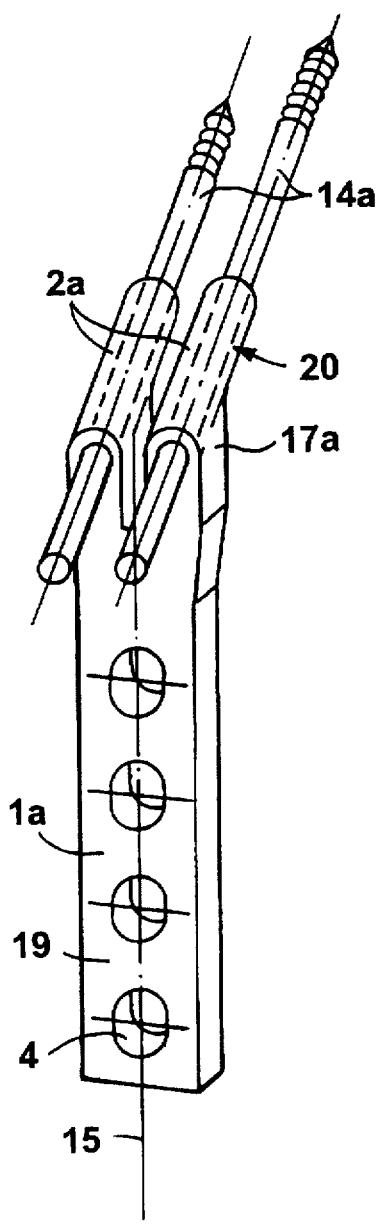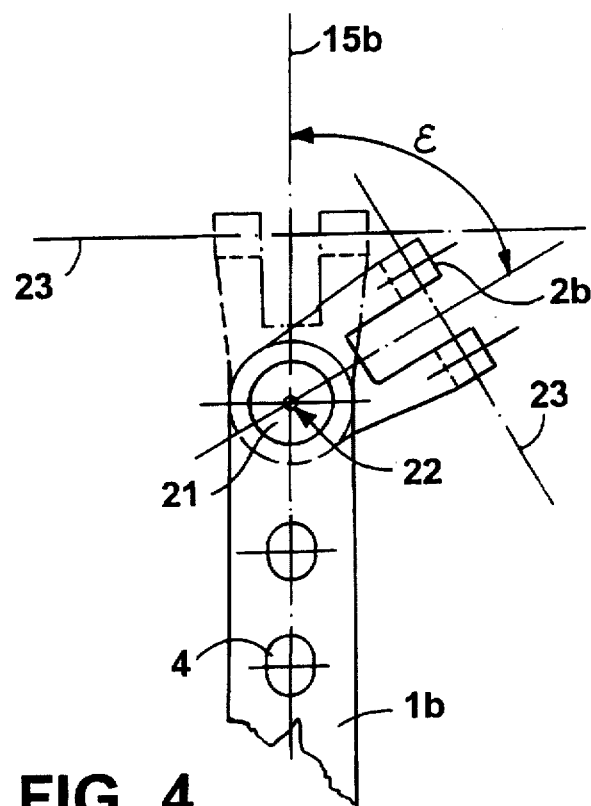
FIG. 3
FIG. 4

FORKED PLATE

FIELD OF THE INVENTION

This invention relates to an angled forked bone plate and in particular, an angled bone plate having a plurality of prongs adaptable to a variety of applications.

BACKGROUND OF THE INVENTION

Angled forked bone plates are generally suited for treatment of fractures and for osteotomies, particularly on the proximal and distal femur, on the proximal tibia and on the proximal humerus, or for arthrodeses at all joints.

Matching the multiplicity of options for application, the number of different versions of such forked plates is very large, resulting in expensive and complex inventory maintenance and logistics.

For this, the invention affords a remedy. The invention is intended to create a generic-type bone plate that permits adaptation to the various usage options without great expense, even at the intraoperative stage.

SUMMARY OF THE INVENTIONS

In accordance with the invention, a bone plate is provided with a longitudinal shaft section and at least two prongs attached in a forked configuration to one end of the shaft section, said prongs being bent at an angle of 60° to 150° relative to the longitudinal axis of the shaft section and means for lengthening said prongs individually. Additional advantageous configurations of the invention are characterized in the subsidiary claims.

The forklike prongs—depending on the application—are bent at an angle α from 60° to 150° (such as 87°, 95° or 135°) with reference to the longitudinal axis of the shaft section and can be lengthened individually. This can be done in essentially two different ways.

In one configuration, the prongs, at their distal ends, are equipped with devices that permit a lengthening of the prongs by joining them with a longitudinal lengthening piece, such as a lengthening bolt that can be screwed into the appropriately configured prong end.

In another configuration, the prongs are hollow throughout, so that a longitudinal lengthening piece, such as a bone screw, can be screwed into the bone via the distal end of the hollow prongs.

Enabling the prongs to be lengthened results in greatly reduced inventory maintenance (fewer models are needed, and in principle even a single universally applicable and adaptable model suffices).

In one preferred configuration of the invention, the prongs bifurcate even before the shaft section ends, preferably at least 1 mm before the prongs are bent at angle α from the longitudinal axis. The degree of the early bifurcation of the prongs depends on the plate design and dimensions, and particularly on the thickness of the shaft section. In relation to the latter, the prongs most appropriately should originate at a point at least 0.1, and preferably 0.3, of the thickness of the shaft section before the bending site.

The early bifurcation of the prongs in the longitudinal shaft section results in better stability of the plate, as well as in an overall improved fracture and bending stability.

The optimal number of prongs is governed by the application of the forked plate; as a rule, two-pronged plates are preferred. However, bone plates having at least three prongs, in which the prongs do not all lie in a common plane, are also contemplated. The size of the free space between the individual prongs likewise depends on the area of application; preferably it should be at least half the smallest diameter of the prongs. In order for a bone screw to be fitted in between the two prongs, the space should be most appropriately at least 3 mm, and preferably 5 mm. The bone screw can be placed through one of the upper boreholes of the shaft section diagonally upwards between the two central prongs, resulting in a particularly solid triangular structure. For this purpose, at least one, and preferably two, boreholes, placed nearest to the prongs, should be positioned in the shaft section in such a way that they allow an axial bending of the bone screw to be inserted at an angle β from 10°–50° relative to the borehole axis.

The cross sectional profile of the prongs can be polygonal (preferably rectangular), or round. If the prongs are bent at an angle α of about 90°, a square cross-sectional profile is preferred, depending on the local bone structure. If the prongs are bent at an angle α of about 130°, a round cross sectional profile is preferred, depending on the local bone structure.

Preferably, the prongs will have a blunt, elongated end.

The free space between the prongs can also be larger, such as 12 mm or 14 mm, so that there is room between them for a part of an endojoint prosthesis, such as the tibia or femur part of a knee joint prosthesis, or the femur part of a hip prosthesis.

The cross sectional profile of the shaft section, oriented orthogonally to the longitudinal axis, can be configured in various ways, depending on the application; preferably it is trapezoidal, with the shorter base line of the trapezoid facing the prongs. In this way, owing to the reduced bone coverage, healing of the shaft section is improved. For this purpose, it is also possible to structure the surface of the shaft section that is turned toward the prongs and rests on the bone in such a way that a further reduction in the bone contact, preferably a contact surface that is only a point or a plurality of points, is achieved.

However, the cross sectional profile of the shaft section, orthogonal to the longitudinal axis, can also be rail-shaped, to increase its gliding capacity, in the event that the forked plate is used as one part of a movable combination implant, or together with a trochanter base plate.

The configuration of at least one borehole of the shaft section as a compression hole in one or two directions of the longitudinal axis is also advantageous.

Individual boreholes, or all of the boreholes, of the shaft section can also be configured to be conical, tapering toward the prongs. This configuration makes it possible to use bone screws with appropriately configured conical heads, resulting in a rigid connection between screws and plate.

Yet another configuration permits the orthogonal on the plane defined by the prongs to enclose an angle ε deviating from 0° to the longitudinal axis of the shaft section. For this purpose, the shaft section can be provided with a pivot joint, whose pivot axis is perpendicular to the shaft section. One end of the shaft section with the prongs can be bent around this pivot joint at the angle ε relative to the longitudinal axis.

In place of the pivot joint, the prongs can also be configured in such a way that the orthogonal on its common plane runs oblique to the longitudinal axis of the shaft section at an angle ε deviating from 0°.

In yet another configuration, the width and/or thickness of the shaft section in the area between the holes is smaller than in the hole area. In most instances the shaft section must be adapted to the bone geometry; this allows the area between the holes to be deformed, with the hole area staying unchanged. Thus, no complications arise in inserting the fixation screws.

The advantages obtained through the invention are essentially that the invention-specific bone plate can be inserted with little force and little damage to the corticalis, using simple techniques, into the bone being treated. It is also rotationally stable.

BRIEF DESCRIPTION OF THE DRAWINGS

The invention will be further described with reference to the accompanying drawings in which:

The invention, and additional forms of the invention, are described in greater detail below, using partly schematic presentations of several configurational examples.

Figures 1, 1A:
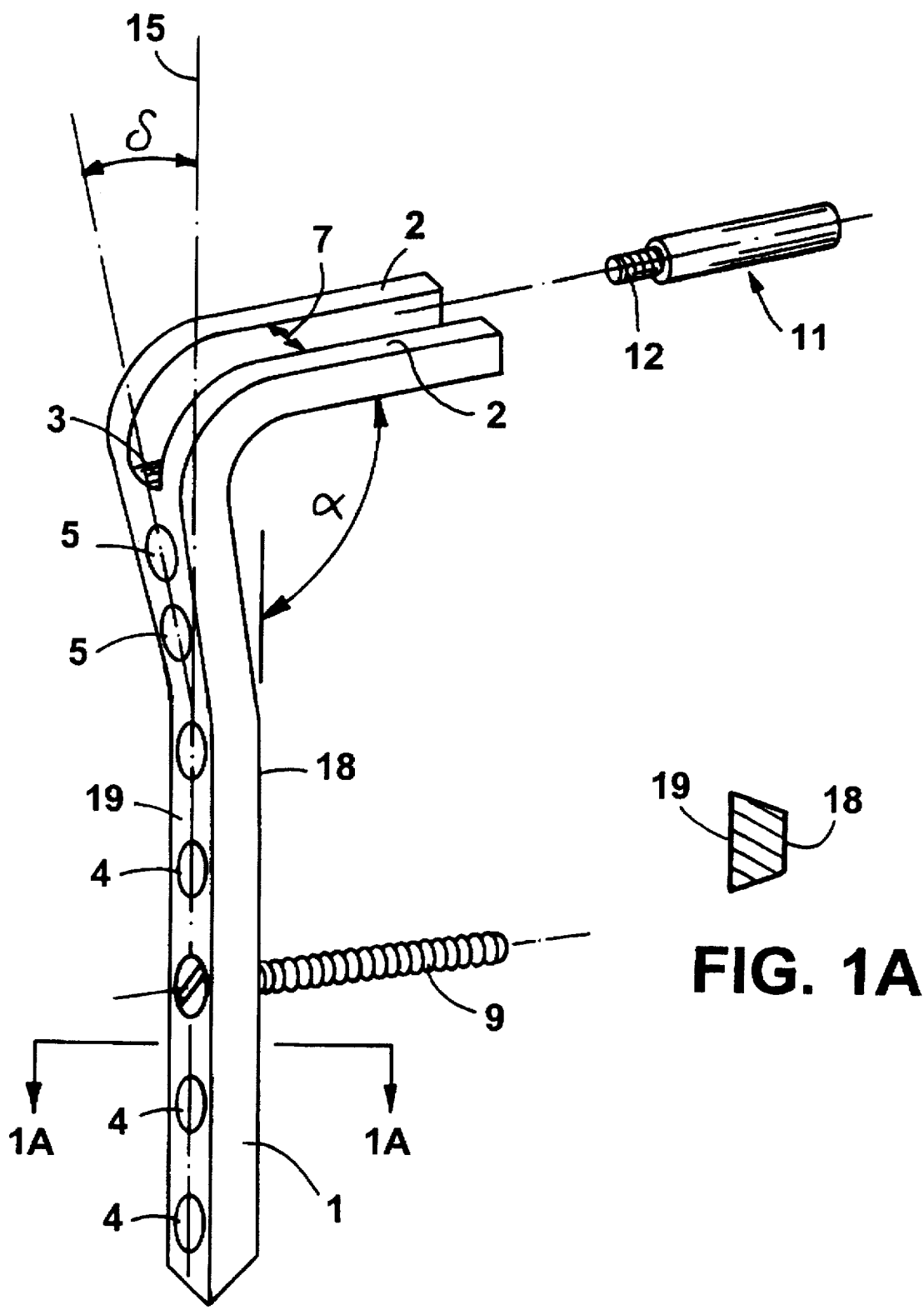

Shown are:

FIG. 1 is a perspective view of a bone plate according to the invention.

FIG. 1A is a cross-section, taken orthogonally to the shaft axis of a bone plate according to the invention.

Figure 2:
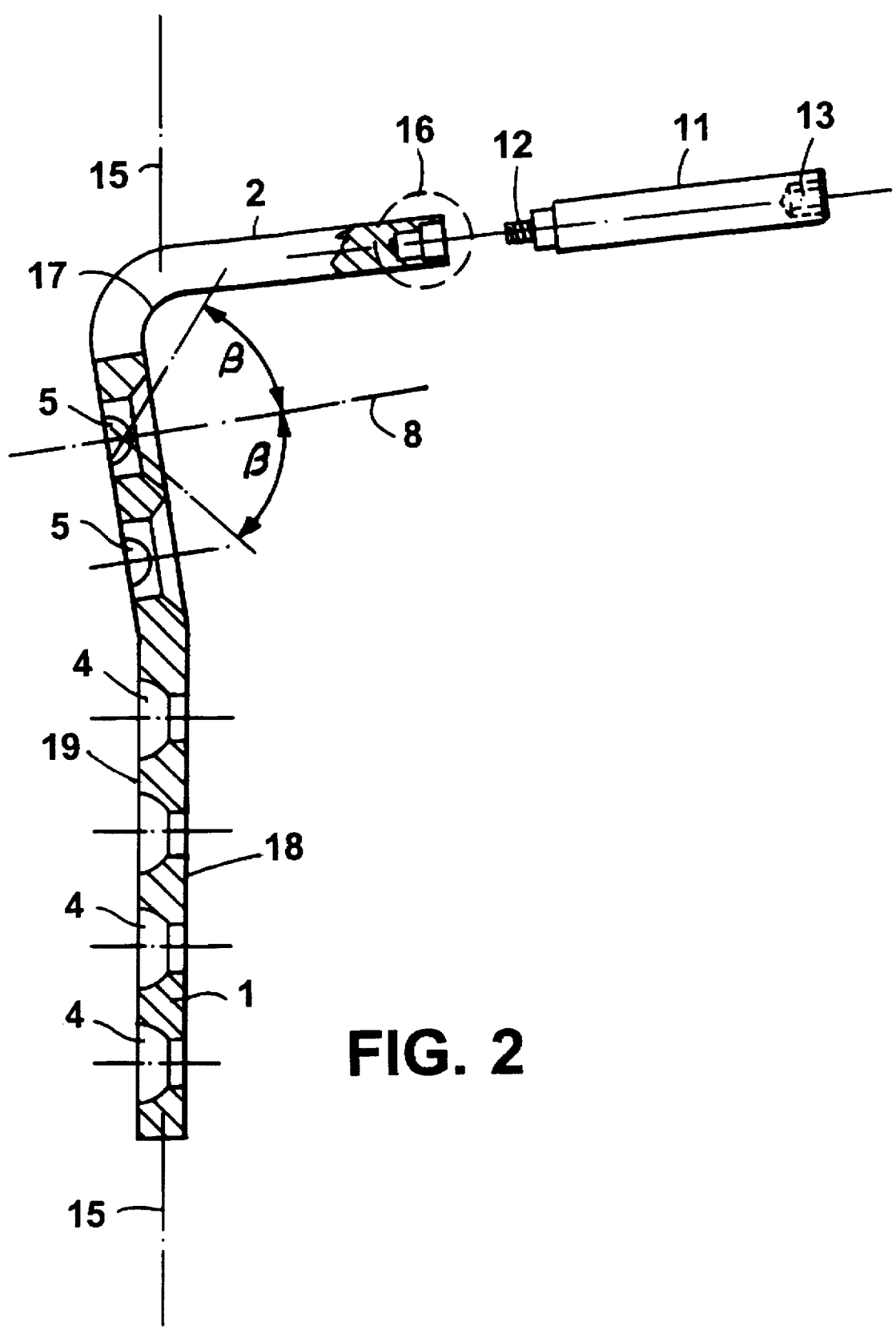

FIG. 2 is a longitudinal section through the bone plate of FIG. 1.

FIG. 3 is a perspective view of another version of the bone plate according to the invention.

FIG. 4 is a partial front elevational view of an additional version of a bone plate according to the invention.

Figure 5:
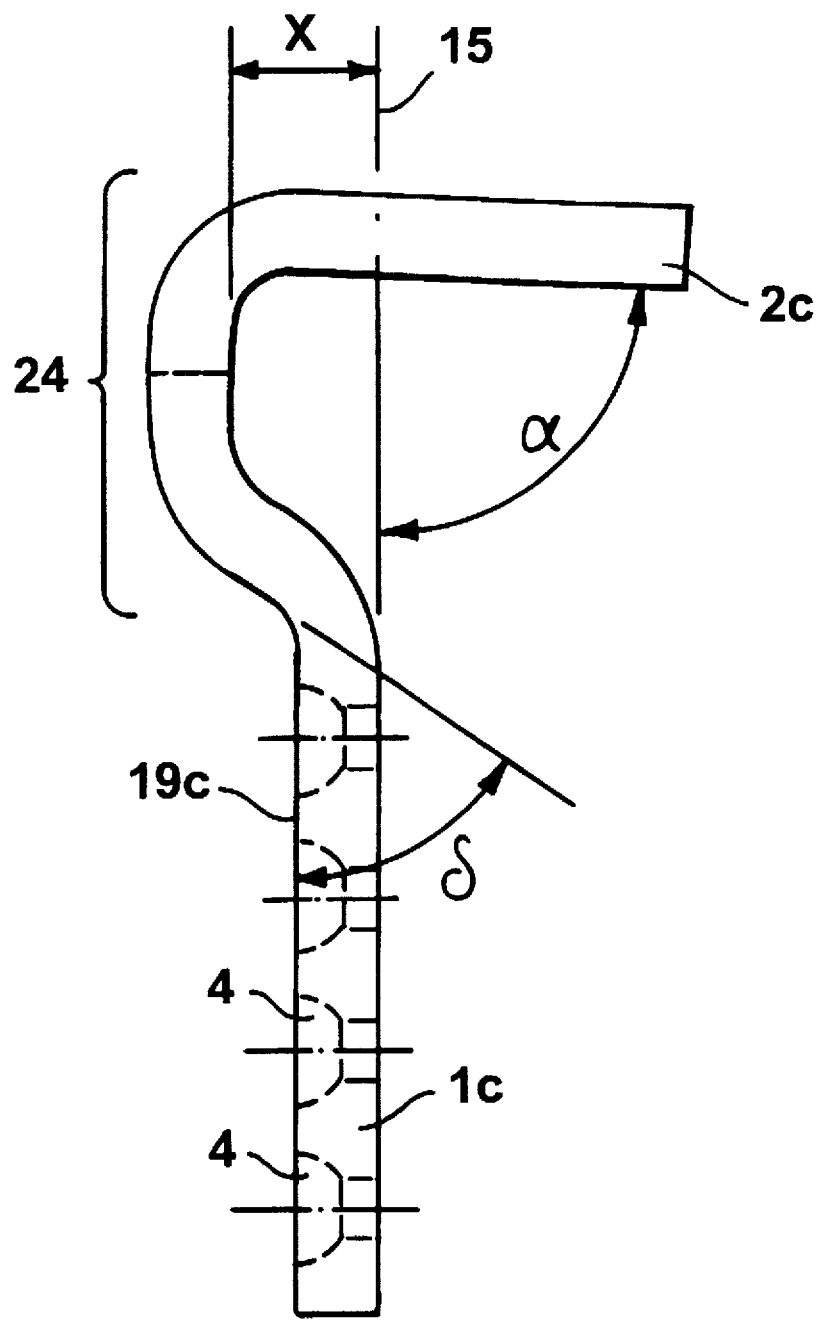

FIG. 5 is a longitudinal section through an additional version of the bone plate according to the invention.

DESCRIPTION OF THE PREFERRED EMBODIMENTS

The bone plate depicted in FIGS. 1 and 2 essentially consists of a longitudinal shaft piece 1, at one end of which two prongs 2 are attached in forked fashion. They are bent at an angle α of about 90° relative to the shaft axis 15.

The shaft section 1 has a surface 18 facing the bone and a surface 19 facing away from the bone, perforated by a number of through-running boreholes 4,5 to admit attachment screws 9. The upper, prong-facing part of the shaft is bent back at an angle δ of 15° in the direction of the surface 19 facing away from the bone, to attain a better fit to the anatomy of the femur.

The two boreholes 5 placed closest to the prongs 2, as is evident in FIG. 2, are configured in such a way as to permit bilateral axial angling of the attachment screws 9 to be inserted at an angle β of up to 50° relative to borehole axis 8. For this purpose, the two upper boreholes 5 widen out from the plate axis 15 both to the surface 18 adjoining the bone and to the surface 19 facing away from the bone, in the form of a hyperboloid.

At their distal ends, the prongs 2 are equipped with devices 16 in the form of a hollow threading, into which a longitudinal lengthening piece 11 can be screwed, having a corresponding threading 12 at one of its ends. At its other end, lengthening piece 11 has a gripping element 13, for example in the form of a hexagonal socket for a matching screw driver. This screw driver can be used to screw lengthening piece 11 into the prong 2. Using a set of lengthening pieces 11 with varying lengths, the prongs 2 can be lengthened individually, depending on how the forked plate is to be used.

The two prongs 2 may bifurcate 3 even before the end of shaft section 1, and in fact about 2 mm before the bending point 17. With a shaft thickness of 6 mm, this constitutes 0.33 of the shaft thickness. The two prongs are separated by free space 7.

The two prongs may have a square cross sectional profile, each side of the square being 6 mm long.

FIG. 1A illustrates a bone plate of the invention which has a trapezoidal cross section taken orthogonally to the longitudinal axis of the plate. The shorter baseline surface 18 faces the prongs 2 of the bone plate, while the longer baseline surface 19 faces away from the prongs.

FIG. 3 depicts another configurational example. In this case, lengthening of the prongs 2a is accomplished by making the prongs 2a hollow, so that appropriate bone screws 14a can be inserted through them. The open channels 20 running through the prongs 2a start at the bending point 17a and end at the blunt end of the prongs 2a. The channels 20 can admit parallel-moving, compressed or closed bone screws 14a, which can be screwed into the bone via the distal end of the hollow prongs 2a, in order to lengthen them. Otherwise, the shaft section 1a is configured analogous to the configuration of FIGS. 1 and 2, except for angle δ, which is 0° in this case, and angle α, which here is 135°, neither of these angles being specifically shown in FIG. 3.

FIG. 4 shows yet another configuration, in which shaft section 1b has a pivot joint 21, whose pivot axis 22 is perpendicular to shaft section 1b. One end of the shaft section with the prongs 2b can be bent around this pivot axis at the angle ε relative to longitudinal axis 15b. The angle ε is formed by the orthogonal of the connection plane 23 between the two prongs 2b and the longitudinal axis 15b of shaft section 1b.

FIG. 5 shows yet another configuration, in which the upper part of shaft section 1c that faces the prongs, is bent back at angle δ from 5° to 15° in the direction of surface 19c that faces away from the bone. It then transitions, in the shape of arcuate section, 24 (with mass X) into the prongs 2c. This design is particularly suited for osteotomies on the proximal femur.

We claim:

1. Bone plate having a longitudinal shaft section with a longitudinal axis and at least two prongs shaped in forked fashion unitary with one end of said shaft section, said prongs having a free space therebetween and being bent at an angle of 60° to 150° relative to said longitudinal axis, and means for lengthening said prongs individually.

2. Bone plate according to claim 1, wherein the prongs have distal ends, said distal ends comprising said means for lengthening.

3. Bone plate according to claim 1, wherein the prongs are hollow for receiving bone screws which when extended through the hollow prongs, lengthen the prongs.

4. Bone plate according to claim 1, wherein the prongs begin before the point at which the plate is bent.

5. Bone plate according to claim 4, wherein the prongs begin at least 1 mm before the point at which the plate is bent.

6. Bone plate according to claim 4, wherein the prongs begin at a point which is at least 0.1 times the thickness of the shaft section from the point at which the plate is bent.

7. Bone plate according to claim 6, wherein the prongs begin at a point which is at least 0.3 times the thickness of the shaft section before the point at which the plate is bent.

8. Bone plate according to claim 1, wherein the free space is at least 3 mm.

9. Bone plate according to claim 8 wherein the free space is at least 5 mm.

10. Bone plate according to claim 8, wherein the free space is at least 12 mm.

11. Bone plate according to claim 8 wherein the free space is at least 14 mm.

12. Bone plate according to claim 8, wherein the free space is at least half the smallest diameter of the prongs.

13. Bone plate according to claim 1, wherein the shaft section has boreholes for receiving attachment screws.

14. Bone plate according to claim 13, wherein at least one borehole adjacent to the prongs has a central axis and is shaped to permit insertion of an attachment screw at an angle of from 10° to 50° relative to said central axis.

15. Bone plate according to claim 13, wherein at least one borehole is a compression hole.

16. Bone plate according to claim 13, wherein at least one borehole has a conical shape tapering toward the prongs.

17. Bone plate according to claim 1, wherein the cross-section of the shaft section, orthogonal to the longitudinal axis of the shaft section, has a trapezoidal shape, with the shorter baseline facing the prongs.

18. Bone plate according to claim 1, wherein the cross-section of the shaft section, orthogonal to its longitudinal axis, is rectangular.

19. Bone plate according to claim 1, wherein the plate has exactly two prongs.

20. Bone plate according to claim 1, wherein the prongs have a polygonal cross section.

21. Bone plate according to claim 1, wherein the prongs have a round cross section.

22. Bone plate according to claim 1, wherein the prongs have a blunt end.

23. Bone plate according to claim 1 wherein the prongs define a plane and a line orthogonal to said plane forms an angle with the longitudinal axis of the shaft section which is other than 0°.

24. Bone plate according to claim 23 wherein the shaft section has a pivot point with an axis perpendicular to the shaft section and around which the end of the shaft section having the prongs can be bent relative to the longitudinal axis.

25. Bone plate according to claim 1 wherein the prong side part of the shaft section is bent back at an angle of from 5° to 15° in the direction of the surface of the shaft section facing away from the bone.

26. Bone plate according to claim 1 wherein the prong side part of the shaft section is arcuate.

27. Bone plate according to claim 1 comprising a plurality of pieces.

28. Bone plate having a longitudinal shaft section with a longitudinal axis and at least two prongs shaped in forked fashion unitary with one end of said shaft section, said prongs being bent at an angle of 60° to 150° relative to said longitudinal axis, said prongs having distal ends comprising means for lengthening said prongs individually, wherein the means for lengthening comprises a threaded socket, said plate further comprising a longitudinal lengthening element equipped at one end with a thread matching the thread of said socket and at its other end with a tool recess to be used to screw the element in the socket.

* * * * *